United States Patent
Trampuz et al.

(10) Patent No.: US 8,076,117 B2
(45) Date of Patent: Dec. 13, 2011

(54) MICROBIAL BIOFILM REMOVAL METHODS AND SYSTEMS

(75) Inventors: Andrej Trampuz, Basel (CH); Robin Patel, Rochester, MN (US); James F. Greenleaf, Rochester, MN (US); Arlen D. Hanssen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 2105 days.

(21) Appl. No.: 11/083,196

(22) Filed: Mar. 17, 2005

(65) Prior Publication Data

US 2005/0241668 A1    Nov. 3, 2005

Related U.S. Application Data

(60) Provisional application No. 60/554,460, filed on Mar. 18, 2004.

(51) Int. Cl.
*C12N 1/00* (2006.01)
*B08B 6/00* (2006.01)
*C11D 3/02* (2006.01)
*C11D 3/20* (2006.01)

(52) U.S. Cl. .............. 435/243; 134/1; 134/1.1; 510/108; 510/109; 510/161

(58) Field of Classification Search .................... 435/243
See application file for complete search history.

(56) References Cited

U.S. PATENT DOCUMENTS

| | | | |
|---|---|---|---|
| 4,193,818 A | 3/1980 | Young et al. | |
| 4,572,203 A | 2/1986 | Feinstein | |
| 5,312,813 A | 5/1994 | Costerton et al. | |
| 5,462,644 A | 10/1995 | Woodson | |
| 5,552,133 A | 9/1996 | Lambert et al. | |
| 5,855,865 A | 1/1999 | Lambert et al. | |
| 5,877,243 A * | 3/1999 | Sarangapani | 524/139 |
| 5,925,257 A | 7/1999 | Albelda et al. | |
| 6,004,438 A | 12/1999 | Woodson | |
| 6,027,572 A | 2/2000 | Labib et al. | |
| 6,258,249 B1 | 7/2001 | Simpson | |
| 6,348,186 B1 | 2/2002 | Sutton et al. | |
| 6,447,718 B1 | 9/2002 | Carter et al. | |
| 6,475,434 B1 | 11/2002 | Darouiche | |

(Continued)

FOREIGN PATENT DOCUMENTS

WO    WO 02/31184 A2    4/2002

OTHER PUBLICATIONS

Lindsay, et al., 1997, Food Microbiology, 14, 383-390.*

(Continued)

*Primary Examiner* — Ruth A Davis
*Assistant Examiner* — Sheridan MacAuley
(74) *Attorney, Agent, or Firm* — Mueting, Raasch & Gebhardt, P.A.

(57) ABSTRACT

Methods, kits, and systems for removing microbial biofilms from surfaces of objects (such as, e.g., explanted medical devices) are disclosed. The methods, kits, and systems rely on the use of acoustic energy in the presence of microbubbles to enhance biofilm removal while retaining viability of the microorganisms in the biofilm. The microbubbles may be provided in a variety of manners such as, e.g., vortexing a liquid, obtaining a suspension that includes pre-formed protein-stabilized microbubbles, etc.

7 Claims, 3 Drawing Sheets

U.S. PATENT DOCUMENTS

| | | | |
|---|---|---|---|
| 6,524,827 | B2 | 2/2003 | Moller et al. |
| 2002/0091424 | A1 | 7/2002 | Biel |
| 2003/0065292 | A1 | 4/2003 | Darouiche et al. |
| 2003/0104359 | A1* | 6/2003 | Cuthbertson et al. ............. 435/5 |

OTHER PUBLICATIONS

Anderl et al., "Role of Nutrient Limitation and Stationary-Phase Existence in *Klebsiella pneumoniae* Biofilm Resistance to Ampicillin and Ciprofloxacin," *Antimicrob. Agents Chemother.*, Apr. 2003;47(4):1251-1256.

Bergamini et al., "Identification of *Staphylococcus epidermidis* vascular graft infections: A comparison of culture techniques," *J. Vasc. Surg.*, May 1989;9(5):665-670.

"BioSurface Technologies CDC Biofilm Reactor with Stir Plate (120 VAC)," datasheet [online]. Cytergy, LLC, 2003, [retrieved on Dec. 28, 2005]. Retrieved from the Internet:<URL:http//www.cytergy.com/cgi-bin/cytergy/cdc_biofim_reactor.html; 2 pgs.

Cardo et al., "Central Sterile Supply," *Hospital Epidemiology and Infection Control 2e.*, 1999:1023-1030.

Costerton et al., "Bacterial Biofilms: A Common Cause of Persistent Infections," *Science*, May 21, 1999;284:1318-1322.

Dobbins et al., "Bacterial Colonization of Orthopedic Fixation Devices in the Absence of Clinical Infection," *J. Infect. Dis.*, Jul. 1988;158(1):203-205.

Donlan, "Biofilms and Device-Associated Infections," *Emerg. Infect. Dis.*, Mar.-Apr. 2001;7(2):277-281.

Donlan et al., "Protocol for Detection of Biofilms on Needleless Connectors Attached to Central Venous Catheters," *J. Clin. Microbiol.*, Feb. 2001;39(2):750-753.

Donlan et al., "Biofilms: Survival Mechanisms of Clinically Relevant Microorganisms," *Clin. Microbiol. Rev.*, Apr. 2002;15(2):167-193.

Gorman et al., "Incidence and nature of peritoneal catheter biofilm determined by electron and confocal laser scanning microscopy," *Epidemiol. Infect.*, 1994; 112:551-559.

Greenleaf et al., "Artificial Cavitation Nuclei Significantly Enhance Acoustically Induced Cell Transfection," *Ultrasound Med. Biol.*, 1998;24(4):587-595.

Jatzwauk et al., "How to improve instrument disinfection by ultrasound," *J. Hosp. Infect.*, 2001;48(Suppl. A):S80-S83.

Johansen et al., "Enzymatic Removal and Disinfection of Bacterial Biofilms," *Appl. Environ. Microbiol.*, Sep. 1997;63(9):3724-3728.

Johnson et al., "Treatment of bacterial biofilms on polymeric biomaterials using antibiotics and ultrasound," *J. Biomater. Sci., Polym. Edn.*, 1998;9(11):1177-1185.

Jyoti et al., "Hybrid cavitation methods for water disinfection: simultaneous use of chemicals with cavitation," *Ultrasonics Sonochemistry*, 2003;10:255-264.

Keane et al., "Characterization of biofilm and encrustation on ureteric stents in vivo," *Br. J. Urol.*, 1994;73:687-691.

Kite et al., "Evaluation of a novel endoluminal brush method for in situ diagnosis of catheter related sepsis," *J. Clin. Pathol.*, 1997;50:278-282.

Maki et al., "A Semiquantitative Culture Method for Identifying Intravenous-Catheter-Related Infection," *N. Engl. J. Med.*, Jun. 9, 1977;296(23):1305-1309.

Nguyen et al., "Detecting Bacterial Colonization of Implanted Orthopaedic Devices by Ultrasonication," *Clin. Orthop. Rel. Res.*, 2002;403:29-37.

Ogden et al., "Principles of Shock Wave Therapy," *Clin. Orthop. Rel. Res.*, Jun. 2001;387:8-17.

"OPTISON Product Description. The next generation of contrast technology" datasheet [online]. General Electric Company, 1997-2006, [retrieved on Aug. 28, 2006]. Retrieved from the Internet<URL:http://www.amershamhealth-us.com/optison/monograph/om03-01.html>; 2 pgs.

"Overview of Regulations," [online]. U.S. Food and Drug Administration, Center for Devices and Radiological Health [retrieved on Oct. 5, 2006]. Retrieved from the Internet<fda.gov/cdrh/devadvice/overview.html>; 4 pgs.

Padberg et al., "Optimal Method for Culturing Vascular Prosthetic Grafts," *J. Surg. Res.*, 1992;53:384-390.

Pitt et al., "Ultrasonic Enhancement of Antibiotic Action on Gram-Negative Bacteria," *Antimicrob. Agents Chemother.*, Nov. 1994;38(11):2577-2582.

Pitts et al., "A microtiter-plate screening method for biofilm disinfection and removal," *J. Microbiol. Methods*, 2003;54:269-276.

Qian et al., "Effect of low-intensity ultrasound upon biofilm structure from confocal scanning laser microscopy observation," *Biomaterials*, 1996;17:1975-1980.

Qian et al., "The Effect of Ultrasonic Frequency upon Enhanced Killing of *P. aeruginosa* Biofilms," *Ann. Biomed. Eng.*, 1997;25:69-76.

Rediske et al., "Ultrasonic Enhancement of Antibiotic Action on *Escherichia coli* Biofilms: an in Vivo Model," *Antimicrob. Agents Chemother.*, May 1999; 43(5):1211-1214.

Rediske et al., "Pulsed Ultrasound Enhances the Killing of *Escherichia coli* Biofilms by Aminoglycoside Antibiotics in Vivo," *Antimicrob. Agents Chemother.*, Mar. 2000;44(3):771-772.

Reitz, "The Sound of Sterilization," *Medical Design News*, Jul./Aug. 2003:32-34.

Sherertz et al., "Three-Year Experience with Sonicated Vascular Catheter Cultures in a Clinical Microbiology Laboratory," *J. Clin. Microbiol.*, Jan. 1990;28(1):76-82.

Tenney et al., "Adherent Microorganisms on Lumenal Surfaces of Long-term Intravenous Catheters. Importance of *Staphylococcus epidermidis* in Patients With Cancer," *Arch. Intern. Med.*, Oct. 1986;146;1949-1954.

Tollefson et al., "Surface Biofilm Disruption. Enhanced Recovery of Microorganisms from Vascular Prostheses," *Arch. Surg.*, Jan. 1987;122:38-43.

Trampuz et al., "A Prospective Comparative Study of Culture of Joint Fluid, Periprosthetic Tissue and Explant Ultrasonicate for the Diagnosis of Total Knee Arthroplasty Infection," $40^{th}$ Annual Meeting of IDSA, Oct. 24-27, 2002, Chicago, IL, Abstract No. 279, 1 pg.

Trampuz et al., "A Prospective Comparative Study of Culture of Synovial Fluid, Periprosthetic Tissue and Explant Sonicate for the Diagnosis of Prosthetic Joint Infection," Nov. 26, 2003, 2 pgs.

Trampuz et al., "Molecular and Antibiofilm Approaches to Prosthetic Joint Infection," *Clin. Orthop. Rel. Res.*, Sep. 2003;414:69-88.

Trampuz et al., "Removal of 3-day-old *Staphylococcus epidermidis* Biofilm from Stainless Steel (SS) and Polymethylmethacrylate (PMMA) Coupons," American Society for Microbiology Conference on Biofilms 2003, Nov. 1-6, 2003, Victoria, B.C., Canada, Abstract #73(A), 1 pg.

Trampuz et al., "Comparison of Scraping, Sonication and Vortexing for Removal of *Staphylococcus epidermidis* Biofilms from Polycarbonate Coupons," American Society for Microbiology Conference on Biofilms 2003, Nov. 1-6, 2003, Victoria, B.C., Canada, Abstract, 1 pg.

Tunney et al., "Improved detection of infection in hip replacements. A currently underestimated problem," *J. Bone Joint Surg.*, Jul. 1998;80-B(4):568-572.

Tunney et al., "Detection of Prosthetic Hip Infection at Revision Arthroplasty by Immunofluorescence Microscopy and PCR Amplification of the Bacterial 16S rRNA Gene," *J. Clin. Microbiol.*, Oct. 1999;37(10):3281-3290.

Wengrovitz et al., "Sonication Provides Maximal Recovery of *Staphylococcus epidermidis* from Slime-Coated Vascular Prosthetics," *Am. Surg.*, Mar. 1991; 57(3):161-164.

Yang et al., "Quantifying biofilm structure using image analysis," *J. Microbiol. Methods*, 2000;39:109-119.

Yang et al., "Evaluation of Biofilm Image Thresholding Methods," *Wat. Res.*, 2001;35(5):1149-1158.

\* cited by examiner

MICROBIAL BIOFILM REMOVAL METHODS AND SYSTEMS

RELATED APPLICATIONS

The present application claims the benefit of U.S. Provisional Application No. 60/554,460, titled MICROBIAL BIOFILM REMOVAL METHODS AND SYSTEMS, filed on Mar. 18, 2004, which is hereby incorporated by reference in its entirety.

The present invention relates to methods, systems, and kits for removing microbial biofilms from surfaces.

Microorganisms commonly attach to surfaces and produce extracellular matrix to form biofilms, the preferred mode of microbial growth in medical, industrial, and natural environments. Growth in biofilms represents a basic survival mechanism by which microorganisms resist environmental influences, antimicrobial killing, and host immune responses. Increased use of indwelling medical devices (e.g., orthopedic devices, neurovascular shunts, prosthetic heart valves, cardiac pacemakers, contact lenses, intrauterine devices, vascular, peritoneal and urinary catheters, etc.) is paralleled by a growing risk of development of biofilm-associated infections on such devices.

One of the primary issues in accurately treating such infections lies in the specific identification of the microorganism (or microorganisms) in the biofilm. Based on this information, for example, appropriate antimicrobial therapy can be selected. Culturing the microorganisms typically requires that they be removed from the surface of the device in a viable state. Removal that results in loss of microbial viability may lower the sensitivity of a culture-based diagnostic test.

Sonication, vortexing, scraping, rolling, flushing, rinsing, brushing, and brushing have been used to dislodge microbial biofilms from a variety of surfaces on, e.g., explanted orthopedic devices, vascular catheters, vascular grafts, ureteric stents, peritoneal catheters, needleless connectors, and membrane filters.

Among the problems associated with the known methods of dislodging microorganisms from biofilms is either destruction of the viability of the microorganisms or removal of insufficient amounts of the microorganisms to allow for culturing and identification. In addition, the parameters of the individual procedure for optimally removing, but not destroying, microorganisms for clinical diagnostic purposes have not been determined for most such processes due to, e.g., their inherent variability.

Other issues that may arise in connection with known methods include, e.g., impractical, non-standardized, or labor-intensive procedures (e.g. scraping, rolling, etc.) and risk of microbial contamination such that mis-identification of the microorganisms may occur.

SUMMARY OF THE INVENTION

The present invention provides methods, kits, and systems for removing microbial biofilms from surfaces of objects such as, e.g., explanted medical devices. The methods, kits, and systems rely on the use of acoustic energy in the presence of microbubbles to enhance biofilm removal while retaining viability of the microorganisms in the biofilm. The microbubbles may be provided in a variety of manners such as, e.g., vortexing a liquid, obtaining a suspension that includes pre-formed protein-stabilized microbubbles, etc. Preferably, however, the acoustic energy is provided after the microbubbles are present in a liquid in which the biofilm is immersed.

Providing microbubbles in a liquid (by, e.g., vortexing, etc) prior to sonication removes more microorganisms from a biofilm than if same procedures are performed in the reverse order or used alone. By dislodging adherent biofilm microorganisms from surfaces, the sensitivity of diagnostic assays and antimicrobial treatment efficacy may be significantly increased. Free-floating planktonic organisms are more likely to be cultured using conventional approaches and are easier to kill than are their sessile counterparts.

Although not wishing to be bound by theory, it is postulated that as ultrasound waves radiate through the liquid, they produce high and low pressure areas. In the low pressure phase, microscopic vapor bubbles are formed in the liquid (a process sometimes referred to as cavitation). During the high pressure stage, the microscopic vapor bubbles in the liquid may collapse or implode, releasing an enormous amount of energy on the surface of the object. This agitation may cause a vacuum-scrubbing action by releasing acoustic energy at the surface of the object. Providing microbubbles in the liquid before introducing acoustic energy may supply microbubble cavitation nuclei that enhance the cavitation effect of subsequent sonication.

Potential advantages of the present invention may include, e.g., improvements in the removal of biofilms from object surfaces, i.e., the present invention may increase the numbers of microorganisms removed from the biofilms. The removal may preferably also retain the viability of a biologically significant portion of the removed microorganisms such that they can be cultured by conventional techniques.

In those embodiments in which the biofilm removal is performed in a sealed, sterile container, the present invention may also carry a lower risk of microbial contamination than do other removal procedures (scraping, rolling, flushing, rinsing, swabbing, brushing, etc.).

In one aspect, the present invention provides a method of removing a biofilm from a surface by locating an object within a container, wherein a biofilm is located on a surface of the object; providing a liquid within the container; vortexing the container with the object and the liquid located therein; and delivering ultrasonic energy to the liquid during the vortexing, wherein the ultrasonic energy impinges on the surface of the object; wherein at least a portion of the biofilm on the surface is removed from the object.

In another aspect, the present invention provides a method of removing a biofilm from a surface by locating an object within a container, wherein a biofilm is located on a surface of the object; providing a liquid within the container; vortexing the container with the object and the liquid located therein; and delivering ultrasonic energy to the liquid after the vortexing, wherein the ultrasonic energy impinges on the surface of the object; wherein at least a portion of the biofilm on the surface is removed from the object.

In another aspect, the present invention provides a method of removing a biofilm from a surface by locating an object within a container, wherein a biofilm is located on a surface of the object; providing a liquid including microbubbles within the container; and delivering ultrasonic energy to the liquid, wherein the ultrasonic energy impinges on the surface of the object; wherein at least a portion of the biofilm on the surface is removed from the object.

In another aspect, the present invention provides a biofilm removal kit that includes a container having an opening and a cover, wherein the cover forms a liquid-tight seal over the opening when in a closed configuration, wherein the container and the cover are sterile; a selected amount of a sterile liquid in a liquid delivery vessel; and printed instructions directing a user to vortex the sterile liquid before providing ultrasonic energy in the container with the sterile liquid located therein.

In another aspect, the present invention provides a biofilm removal kit that includes a container having an opening and a cover, wherein the cover forms a liquid-tight seal over the opening when in a closed configuration, wherein the container and the cover are sterile; and a selected amount of a sterile liquid including encapsulated microbubbles in a liquid delivery vessel, wherein the encapsulated microbubbles comprise a shell.

These and other features and advantages of the present invention may be described below in connection with various exemplary embodiments of the devices and methods of the present invention.

BRIEF DESCRIPTIONS OF THE FIGURES

DETAILED DESCRIPTION OF EXEMPLARY EMBODIMENTS OF THE INVENTION

Figure 1:
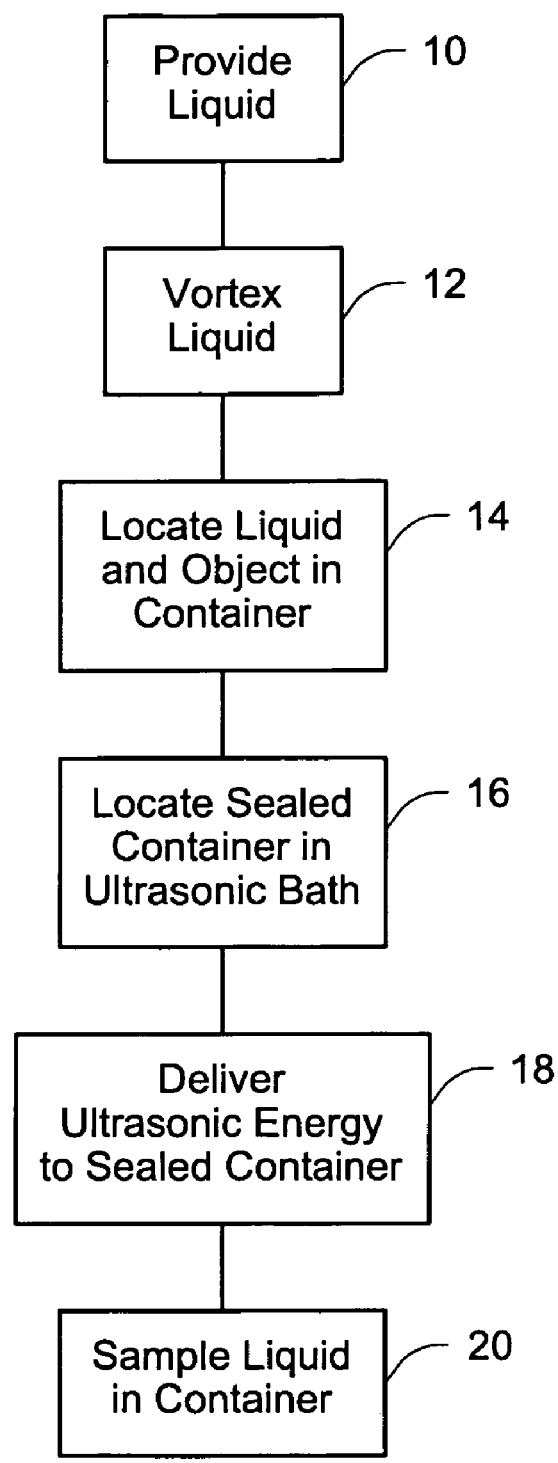
FIG. 1 is a flow chart depicting one exemplary method according to the present invention.

In the following detailed description of some exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

In various aspects, the present invention may provide methods, systems and/or kits for the removal of biofilms from one or more surfaces of an object. It may be preferred that the object be a medical device such as a needleless connector, explanted medical device, etc.

FIG. 1 is flow chart depicting one exemplary embodiment of the methods of the present invention. The method may optionally include, e.g., removal or explantation of an object such as a medical device. Medical devices processed according to the present invention may include, e.g., but are not limited to, orthopedic devices, vascular catheters, vascular grafts, ureteric stents, peritoneal catheters, needleless connectors, membrane filters, contact lenses, etc. As used herein, an "explanted" medical device is a medical device that has been removed from a patient after implantation in the patient. It may be preferred that, before removal of the medical device, the implantation period be one day or more, preferably one week or more. The object to be processed preferably includes one or more surfaces that may have a microbial biofilm formed thereon.

The exemplary method also includes use of a container in which the object to be processed can be placed. It may be preferred that the container be sufficiently large such that it can be closed and sealed with the object located inside. In various embodiments, it may be preferred that the container be rigid, e.g., manufactured from rigid polymers (e.g., polycarbonates, etc.), glass, or other suitable materials such that sharp edges and/or points on the object or objects placed inside of the container cannot puncture or tear the container and pose a biohazardous risk for the environment. In some embodiments, however, containers with flexible walls (e.g., bags, pouches, etc.) may be used in connection with the present invention. In one specific example, the container may be in the form of a rigid polymeric jar that includes a lid with a seal such that the container can closed and sealed to prevent or significantly reduce the likelihood of leaks and risk of microbial contamination.

This exemplary method also includes providing a liquid 10 in which the surface or surfaces containing the biofilm can be immersed. In various embodiments, the liquid may include, e.g., any aqueous or non-aqueous liquid (solution, suspension, mixture, etc.), normal saline (in some instances, the liquid may consist essentially of sterile normal saline), nutrient broths, etc. It may be preferred that the liquid be sterile as delivered to the container. As discussed herein, the present invention may provide advantages by including microbubbles in the liquid before delivering acoustic energy thereto.

In some embodiments, where a more efficient biofilm removal is desired, the cavitation effect may be enhanced by adding sterile beads to the liquid. In other embodiments, biofilm removal efficiency may be enhanced by controlling the temperature of the liquid 10, e.g., increasing the temperature of the liquid to, e.g., at least 30° C., more preferably at least 35° C., and in some instances to 37° C.

In the method of FIG. 1, the microbubbles may preferably be provided by vortexing the liquid 12. The vortexing may be performed before the liquid is delivered to the container or after the liquid is located in the container. If the vortexing is performed while the liquid is in the container that receives the object having a biofilm to be removed, then the vortexing may be performed before the object is placed in the container, e.g., with only the liquid in the container. Alternatively, the vortexing may be performed after the liquid and the object are located within the container. In another alternative, the liquid could first be vortexed in one container and then added to a different container in which the object having a biofilm is located.

The vortexing may be performed by any suitable technique and equipment. For example, the vortexing may be performed using conventional laboratory vortexing equipment (e.g., MINI VORTEXER, VWR Scientific). Other methods of shaking or mixing the liquid that are sufficient to cause the formation of microbubbles in the liquid may be used.

The amount of liquid supplied in the container may be selected such that, at rest, the amount of liquid is sufficient to cover the surfaces of the object in the container. Alternatively, lesser amounts of liquid may be used such that the object is not completely immersed in the liquid. For example, lesser amounts of liquid may be provided if the surfaces from which the biofilm microorganisms are located in areas of the container that do not require the entire object to be immersed in the liquid. One potential advantage of using smaller amounts of liquid may include, e.g., obtaining higher concentrations of any microorganisms removed from the biofilms in the liquid. Those higher concentrations may be beneficial in culturing the microorganisms for identification purposes.

After the vortexed liquid and the object are both located within the container 14 and the container has been sealed, the method proceeds to the delivery of acoustic energy. It may be preferred, for example, that the sealed container be located within an ultrasound bath 16. In other methods, however, the container itself may be directly coupled to or include ultrasonic transducers to deliver acoustic energy into the liquid sealed within the container.

In the method depicted in the flowchart of FIG. 1, ultrasonic energy is delivered 18 to the container through an ultrasonic bath. To accomplish that, ultrasound transducers are preferably located within the bath, such that the ultrasonic energy generated by the transducers passes through the bath liquid before reaching the walls of the container. The acoustic energy then passes through the container walls and into the liquid located within the sealed container. It may be preferred that ultrasonic transducers be located on at least two sides of the container, such that ultrasonic energy is more likely to reach more surfaces of the object located within the container. It may be even more preferred that the ultrasonic transducers are located on opposite sides of the container.

During delivery of the acoustic energy, a number of parameters may be adjusted to enhance removal of viable microorganisms from the biofilms on the object. Those parameters may include, e.g., frequency (typically measured in Hz), ultrasound waveform (e.g., sinusoidal, step, etc.), ultrasound duty cycle (e.g., continuous, pulsed, etc.), energy density (measured in $mW/cm^2$), and duration of the energy delivery. Other variables may include, e.g., the size of the ultrasonic bath, the composition of the bath liquid (e.g., deionized, degassed water), the temperature of the bath liquid, etc.

Delivery of acoustic energy to the bath liquid and, subsequently, to the liquid in the sealed container preferably causes microorganisms in the biofilm to be released into the liquid. As discussed herein, the conditions are preferably such that a biologically significant portion of the microorganisms retain their viability after release from the biofilm.

After delivery of the acoustic energy, the sealed container is removed from the bath and samples of the liquid are obtained 20 to, e.g., quantify and/or identify the microorganisms released from the biofilms. The quantification and/or identification may include, e.g., culturing, molecular techniques, etc.

Figure 2:
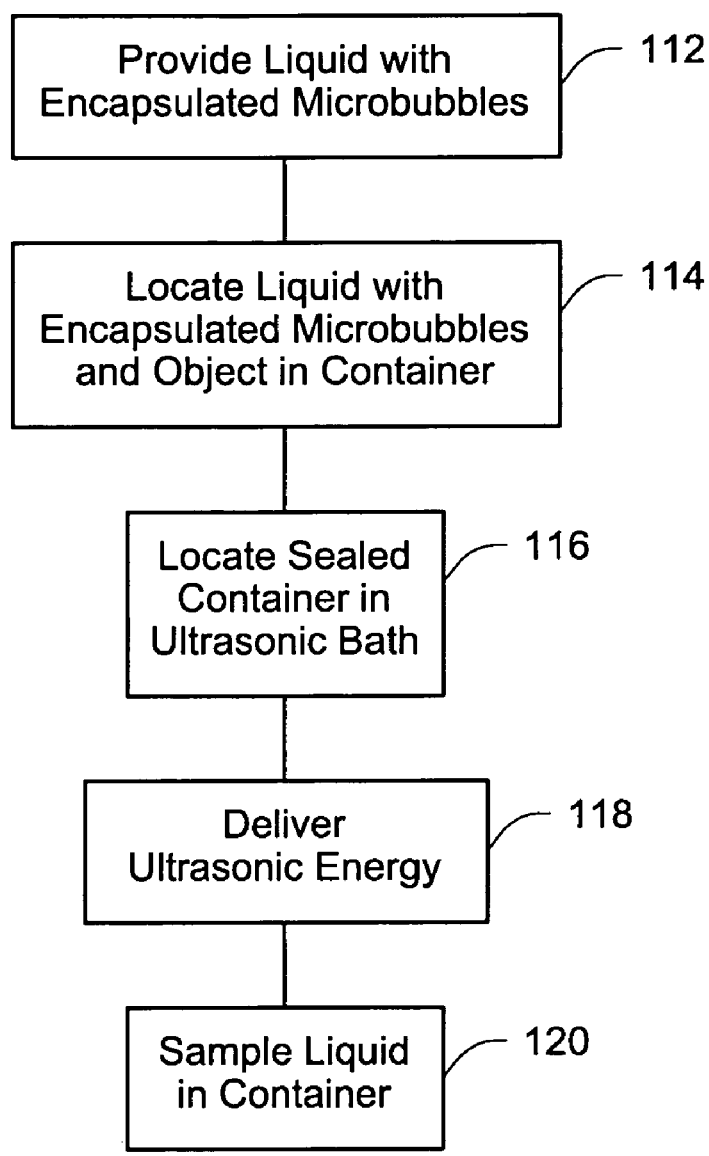
FIG. 2 is a flow chart depicting an alternate exemplary method according to the present invention.

FIG. 2 is a flow diagram of an alternative method according to the present invention in which the liquid provided in the container contains encapsulated microbubbles as provided 112. One example of such a liquid may include, e.g., encapsulated microbubbles that include, e.g., shells. The encapsulated microbubbles may preferably include water-insoluble gas within the shell. Examples of some potentially suitable encapsulated microbubbles may be described in, e.g., U.S. Pat. No. 4,572,203 (Feinstein); U.S. Pat. No. 5,552,133 (Lambert et al.); U.S. Pat. No. 5,855,865 (Lambert et al.); and U.S. Pat. No. 6,348,186 B1 (Sutton et al.). Commercially available products including potentially suitable encapsulated microbubbles may be marketed for ultrasonic imaging, e.g., the product including encapsulated microbubbles marketed under the tradename OPTISON by Amersham Health.

As used in connection with the present invention, the encapsulated microbubbles may preferably include a biocompatible shell, e.g., protein, etc. The shells may, e.g., preferably be formed of one or more proteins capable of forming a film to encapsulate a gas. The encapsulated gas may preferably be a water-insoluble gas such as, e.g., fluorine-containing gases such as sulfur hexafluoride, perfluoroethane, perfluoropropane, perfluoromethane, and perfluorobutane. Such products do not require vortexing to form the encapsulated microbubbles (which are, instead, provided in a relatively stable form in the liquid). It may, however, be beneficial to mix such liquids to re-suspend the encapsulated microbubbles located within the liquid.

The encapsulated microbubble-laden liquid and the object to be processed (e.g., an explanted medical device) are preferably both located in a sealed container 114 as described in connection with the method of FIG. 1. One potential difference is that the carrier liquid in which the encapsulated microbubbles are provided may be supplemented by a second liquid (e.g., normal sterile saline, etc.) if an increased volume of liquid is desired in the container but additional encapsulated microbubbles are not required.

As with the method of FIG. 1, the total amount of liquid supplied in the container may be selected such that, at rest, it is sufficient to cover the surfaces of the object in the container. Alternatively, lesser amounts of liquid may be used such that the object is not completely immersed in the liquid. For example, lesser amounts of liquid may be provided if the surfaces from which the biofilm microorganisms are located in areas of the container that do not require the entire object to be immersed in the liquid. One potential advantage of using smaller amounts of liquid may include, e.g., obtaining higher concentrations of any microorganisms removed from the biofilms in the liquid. Those higher concentrations may be beneficial in culturing the microorganisms for identification purposes.

After the carrier liquid with encapsulated microbubbles and the object are both located within the container 114 and the container has been sealed, the method proceeds to the delivery of ultrasonic energy. It may be preferred, for example, that the sealed container be located within an ultrasonic bath 116.

With the sealed container located within the ultrasonic bath, the ultrasonic energy can be delivered 118. To accomplish that, ultrasonic transducers are preferably located within the bath, such that the ultrasonic energy generated by the transducers passes through the bath liquid before reaching the walls of the container. The ultrasonic energy then passes through the container walls and into the liquid located within the sealed container.

Figure 3:
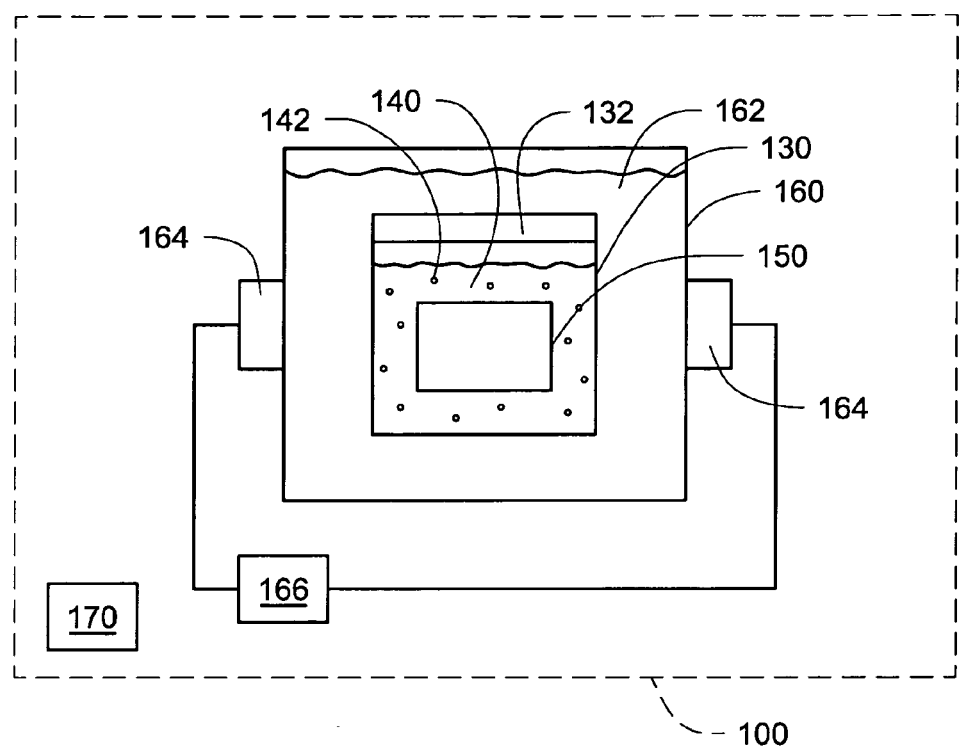
FIG. 3 is a schematic diagram of one exemplary system according to the present invention.

FIG. 3 is a schematic diagram of one exemplary system according to the present invention. The system 100 may preferably include a container 130 with a cover 132 that can form a liquid-tight seal over the opening into the container 130. The container 130 may preferably be sufficiently large such that it can be closed and sealed with an object 150 located inside.

In various embodiments, it may be preferred that the container 130 be rigid, e.g., manufactured from rigid polymers (e.g., polycarbonates, etc.), glass, or other suitable materials such that, e.g., the rigid container is capable of maintaining a fixed, self-supporting shape and such that sharp edges and/or points on the object 150 (or objects) placed inside of the container cannot puncture or tear the container. In some embodiments, however, containers with flexible walls (e.g., bags, pouches, etc.) may be used in connection with the present invention. In one specific example, the container may be in the form of a rigid polymeric jar that includes a lid with a seal such that the container can closed and sealed to prevent or significantly reduce the likelihood of leaks. Suitable containers may be obtained from, e.g., Nalge Nunc International Corporation (marketed under the tradename NALGENE).

The container 130 is depicted as being located within an ultrasonic tank 160 including a bath liquid 162 and ultrasonic transducers 164. The container 130 is, however, preferably removable from the bath 162 for loading and unloading. Although the depicted system 100 includes two ultrasonic transducers 164, it should be understood that as few as one transducer or more than two transducers could be used in connection with the present invention. The transducers 164 are driven, in the depicted embodiment, by a single ultrasonic energy source 166, although it should be understood that two or more energy sources could be connected to the different ultrasonic transducers (e.g., each ultrasonic transducer may be driven by an independent energy source).

The depicted system also includes an optional vortexer 170 that may be used, e.g., to provide microbubbles 142 in the liquid 140 located in container 130. The vortexer 170 may be used to vortex the liquid 140 before it is loaded into the container 130 or after the liquid 140 is located within the container 130.

Regardless of the method used to obtain microbubbles, i.e., whether microbubbles are formed by vortexing alone or whether the liquid includes encapsulated microbubbles with shells, it may be preferred that the interior of the container in which the object and liquid are located be substantially at ambient pressure (e.g., atmospheric pressure). Alternatively, the interior of the container may be held at either negative pressure or at positive pressure (relative to ambient pressure) if so desired. These pressure conditions may be held during vortexing and/or during the delivery of ultrasonic energy. Minimal pressure changes in the interior of the container may be expected during processing according to the methods of the present invention.

Figure 4:
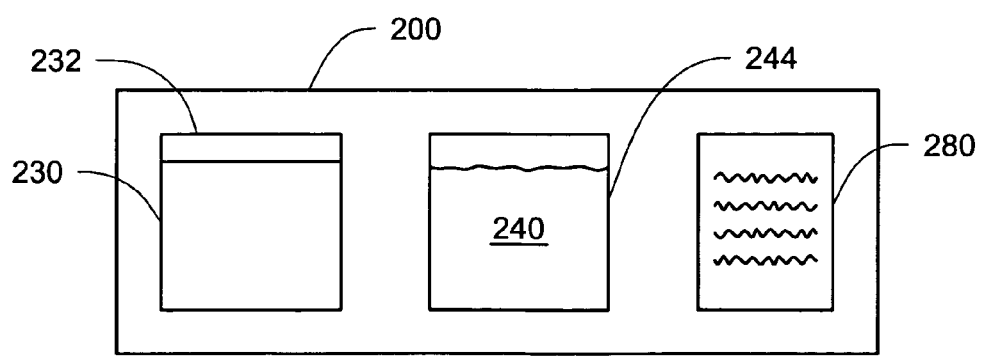
FIG. 4 is a schematic depiction of one exemplary kit according to the present invention.

FIG. 4 is a schematic representation of a kit 200 according to the present invention. The kit 200 may preferably include, e.g., a container 230 with a cover 232 that is capable of forming a liquid-tight seal over the opening into the container 230. The container 230 and cover 232 may be of any suitable construction as described herein, although it may be preferred that they be provided in a sterile condition, possibly in a package that, e.g., prevents biological contamination until opened.

The kit 200 may also preferably include, e.g., a selected amount of liquid 240 in a supply container 244. The liquid 240 may preferably be sterile, e.g., sterile normal saline, etc. In other instances, the liquid may include, e.g., encapsulated microbubbles that include shells, and that may preferably include water-insoluble gas within the shells. Examples of some potentially suitable encapsulated microbubbles may be described in, e.g., U.S. Pat. Nos. 4,572,203 (Feinstein); U.S. Pat. No. 5,552,133 (Lambert et al.); U.S. Pat. No. 5,855,865 (Lambert et al.); and U.S. Pat. No. 6,348,186 B1 (Sutton et al.). Commercially available products including potentially suitable encapsulated microbubbles may be marketed for ultrasonic imaging, e.g., the product including encapsulated microbubbles marketed under the tradename OPTISON by Amersham Health.

The kit 200 may also preferably include printed instructions directing a user to, e.g., vortex the sterile liquid 240 before providing ultrasonic energy in the container 230 with the sterile liquid located therein. Such instructions may direct a user to practice all or a portion of the methods described herein.

All of the components of the kit 200 may be provided in a package such that the different components can be retained together during transport and handling, preferably until use by a medical practitioner.

As used herein and in the appended claims, the singular forms "a," "and," and "the" include plural referents unless explicitly limited to the singular form or the context clearly dictates otherwise.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of removing a biofilm from a surface, the method comprising:
   locating an object within a container, wherein a biofilm is located on a surface of the object;
   providing a liquid comprising microbubbles within the container, wherein providing the liquid comprising microbubbles comprises vortexing the liquid to form the microbubbles, wherein the vortexing is performed while the liquid is outside of the container; and
   delivering ultrasonic energy to the liquid comprising the microbubbles, wherein the ultrasonic energy impinges on the surface of the object;
   wherein at least a portion of the biofilm on the surface is removed from the object.

2. A method of removing a biofilm from a surface, the method comprising:
   locating an object within a container, wherein a biofilm is located on a surface of the object;
   providing a liquid comprising microbubbles within the container, wherein providing the liquid comprising microbubbles comprises vortexing the liquid to form the microbubbles, wherein the vortexing is performed while the liquid is in the container and before the object is located in the container; and
   delivering ultrasonic energy to the liquid comprising the microbubbles, wherein the ultrasonic energy impinges on the surface of the object;
   wherein at least a portion of the biofilm on the surface is removed from the object.

3. A method of removing a biofilm from a surface, the method comprising:
   locating an object within a container, wherein a biofilm is located on a surface of the object;
   providing a liquid comprising microbubbles within the container, wherein the liquid comprises encapsulated microbubbles comprising a shell; and
   delivering ultrasonic energy to the liquid comprising the microbubbles, wherein the ultrasonic energy impinges on the surface of the object;
   wherein at least a portion of the biofilm on the surface is removed from the object.

4. A method of removing a biofilm from a surface, the method comprising:
   locating an object within a container, wherein a biofilm is located on a surface of the object; and
   delivering ultrasonic energy to a liquid within the container, wherein the liquid comprises encapsulated microbubbles comprising a shell and wherein the ultrasonic energy impinges on the surface of the object;
   wherein at least a portion of the biofilm on the surface is removed from the object.

5. The method of claim 4, wherein the shell comprises a biocompatible shell.

6. A method of removing a biofilm from a surface, the method comprising:
   locating an object within a container, wherein a biofilm is located on a surface of the object;
   providing a liquid comprising microbubbles within the container, wherein the microbubbles comprise pre-formed protein-stabilized microbubbles; and
   delivering ultrasonic energy to the liquid comprising the microbubbles, wherein the ultrasonic energy impinges on the surface of the object;
   wherein at least a portion of the biofilm on the surface is removed from the object.

7. The method of claim 6 wherein the microbubbles comprise a shell.

* * * * *